US008426170B2

(12) United States Patent
Stordeur et al.

(10) Patent No.: US 8,426,170 B2
(45) Date of Patent: Apr. 23, 2013

(54) METHOD FOR EVALUATING THE RESPONSE OF AN INDIVIDUAL TO A TREATMENT WITH A TYPE I INTERFERON (IFN)

(75) Inventors: Patrick Stordeur, Forest (BE); Mathieu Vokaer, Beersel (BE); Annick Ocmant, Le Roeulx (BE); Michel Goldman, Uccle (BE)

(73) Assignee: Universite Libre de Bruxelles, Brussels (BE)

( * ) Notice: Subject to any disclaimer, the term of this patent is extended or adjusted under 35 U.S.C. 154(b) by 675 days.

(21) Appl. No.: 12/522,623

(22) PCT Filed: Jan. 24, 2008

(86) PCT No.: PCT/EP2008/050807
§ 371 (c)(1),
(2), (4) Date: Jul. 9, 2009

(87) PCT Pub. No.: WO2008/090196
PCT Pub. Date: Jul. 31, 2008

(65) Prior Publication Data
US 2010/0129788 A1    May 27, 2010

(30) Foreign Application Priority Data

Jan. 25, 2007  (EP) .................................. 07447004

(51) Int. Cl.
*C12P 19/34*        (2006.01)
(52) U.S. Cl.
USPC ....................................................... 435/91.2
(58) Field of Classification Search ................. 435/91.2
See application file for complete search history.

(56) References Cited

FOREIGN PATENT DOCUMENTS

| EP | 1 201 680 | 5/2002 |
|---|---|---|
| WO | WO 2006/086586 | 8/2006 |

OTHER PUBLICATIONS

Jorns et al., Rapid and Simple Detection of IFN-Neutralizing Antibodies in Chronic Hepatitis C Non-Responsive to IFN-a,Journal of Medical Virology 78:74-82 (2006).*
Antonelli et al. Correlation of Interferon-Induced Expression of MxA mRNA in Peripheral Blood Mononuclear Cells with the Response of Patients with Chronic Active Hepatitis C to IFN-a Therapy, Journal of Interferon and Cytokine Research 19:243±251 (1999).*
Towbin et al., A Whole Blood Immunoassay for the Interferon-Inducible Human Mx Protein,Journal of Interferon Research 12:67-74 (1992).*

Bertolotto et al.., Differential effects of three interferon betas on neutralising antibodies in patients with multiple sclerosis: a follow up study in an independent laboratory,J Neurol Neurosurg Psychiatry 2002;73:148-153.*
Pachner et al., Mol. Diagn. vol. 7, No. 1, pp. 17-25, 2003.*
Bertolotto et al., J. Neurosurg. Psychiatry, col. 75, pp. 1294-1299, 2004.*
Ahern, H. The Scientist, vol. 20, No. 15, pp. 1-9, 1995.*
Santos, et al. "Dynamics of Interferon-β Modulated mRNA Biomarkers in Multiple Sclerosis Patients with Anti-Interferon-62 Neutralizing Antibodies," *Journal of Neuroimmunology*, vol. 176, pp. 125-133, 2006.
Gilli, et al. "Evaluation of IFNα Bioavailability by MxA mRNA in HCV Patients," *Journal of Immunological Methods*, vol. 262, pp. 187-190, 2002.
Gneiss, et al. "Interferon-β Antibodies Have a Higher Affinity in Patients with Neutralizing Antibodies Compared to Patients with Non-Neutralizing Antibodies," *Journal of Neuroimmunology*, vol. 174, pp. 174-179, 2006.
Shak, et al. "Gene Expression Profiling of EGFR Positive Cancer," downloaded from http://www.ebi.ac.uk/cgi-bin/emblfetch?style-html&id-dd328666, 1 page, Sep. 20, 2006.
Sørensen, et al. "Guidelines on Use of Anti-IFN-β Antibody Measurements in Multiple Sclerosis: Report of an EFNS Task Force on IFN-β. Antibodies in Multiple Sclerosis," *European Journal of Neurology*, vol. 12, pp. 817-827, 2005.
Pachner, et al. Multiplex Analysis of Expression of Three IFNβ-Induced Genes in Antibody-Positive MS Patients, *Neurology*, vol. 66 pp. 444-446, 2006.
Jorns, et al. "Rapid and Simple Detection of IFN-Neutralizing Antibodies in Chronic Hepatitis C Non-Responsive to IFN-α," *Journal of Medical Virology*, vol. 78, pp. 74-82, 2006.
McKay, et al. "Analysis of Neutralizing Antibodies to Therapeutic Interferon-Beta in Multiple Sclerosis Patients: A Comparison of Three Methods in a Large Australasian Cohort," *Journal of Immunological Methods*, vol. 310, pp. 20-29, 2006.
Anti-Pachner, et al. "The Importance of Measuring IFNβ Bioactivity: Monitoring in MS Patients and the Effect of IFNβ Antibodies," *Journal of Neuroimmunology*, vol. 166, pp. 180-188, 2005.
International Search Report dated Apr. 17, 2008.

* cited by examiner

*Primary Examiner* — Gary Benzion
*Assistant Examiner* — Cynthia Wilder
(74) *Attorney, Agent, or Firm* — Knobbe, Martens, Olson & Bear LLP

(57) ABSTRACT

A method for evaluating the in vivo presence of a factor that prevents the biological effect of a type I (IFN) in an individual that is under treatment with type I interferon is described. The in vivo presence of antibodies directed against a type I interferon (IFN) is evaluated in an individual that is under treatment with type I interferon. The method includes incubating a blood sample of the individual in vitro with a suitable amount of the type I interferon for a suitable period of time, and determining mRNA levels of a biological marker of IFN activity, preferably MxA, in the blood sample. The treatment may involve a treatment of multiple sclerosis, HCV or HBV using a type I interferon.

7 Claims, 4 Drawing Sheets

SEQUENCE LISTING

```
<160> NUMBER OF SEQ ID NOS: 9

<210> SEQ ID NO 1
<211> LENGTH: 23
<212> TYPE: DNA
<213> ORGANISM: artificial sequence
<220> FEATURE:
<223> OTHER INFORMATION: primer

<400> SEQUENCE: 1
acacgagttc cacaaatgga gta                                              23

<210> SEQ ID NO 2
<211> LENGTH: 23
<212> TYPE: DNA
<213> ORGANISM: artificial sequence
<220> FEATURE:
<223> OTHER INFORMATION: primer

<400> SEQUENCE: 2
cgattgtctc aaatgtcctg taa                                              23

<210> SEQ ID NO 3
<211> LENGTH: 25
<212> TYPE: DNA
<213> ORGANISM: artificial sequence
<220> FEATURE:
<223> OTHER INFORMATION: primer

<400> SEQUENCE: 3
tcgtggtaga gagctgccag gcttt                                            25

<210> SEQ ID NO 4
<211> LENGTH: 22
<212> TYPE: DNA
<213> ORGANISM: artificial sequence
<220> FEATURE:
<223> OTHER INFORMATION: primer

<400> SEQUENCE: 4
tgtctgtctg cagattggct ac                                               22

<210> SEQ ID NO 5
<211> LENGTH: 20
<212> TYPE: DNA
<213> ORGANISM: artificial sequence
<220> FEATURE:
<223> OTHER INFORMATION: primer

<400> SEQUENCE: 5
agatggatca gccaagaagg                                                  20

<210> SEQ ID NO 6
<211> LENGTH: 25
<212> TYPE: DNA
<213> ORGANISM: artificial sequence
```

```
-continued

<220> FEATURE:
<223> OTHER INFORMATION: primer

<400> SEQUENCE: 6
cggattacac cttcccactt gctga                                          25

<210> SEQ ID NO 7
<211> LENGTH: 16
<212> TYPE: DNA
<213> ORGANISM: artificial sequence
<220> FEATURE:
<223> OTHER INFORMATION: primer

<400> SEQUENCE: 7
cctttgggct ggtcat                                                    16

<210> SEQ ID NO 8
<211> LENGTH: 17
<212> TYPE: DNA
<213> ORGANISM: artificial sequence
<220> FEATURE:
<223> OTHER INFORMATION: primer

<400> SEQUENCE: 8
gcacttcagg gttgtag                                                   17

<210> SEQ ID NO 9
<211> LENGTH: 22
<212> TYPE: DNA
<213> ORGANISM: artificial sequence
<220> FEATURE:
<223> OTHER INFORMATION: primer

<400> SEQUENCE: 9
ccagcaggtg ttcgacaatg gc                                             22
```

METHOD FOR EVALUATING THE RESPONSE OF AN INDIVIDUAL TO A TREATMENT WITH A TYPE I INTERFERON (IFN)

CROSS-REFERENCE TO RELATED APPLICATIONS

This application is the U.S. National Phase under 35 U.S.C. §371 of International Application PCT/EP2008/050807, filed Jan. 24, 2008, which claims priority to EP 07447004.8, filed Jan. 25, 2007.

TECHNICAL FIELD

The present invention is directed to the medical field. In particular, the present invention is directed to a method for determining the response of an individual to a treatment with a type I interferon (type I IFN), for instance individuals suffering from multiple sclerosis, HCV or HBV. More in particular the invention relates to a method for evaluating the in vivo presence of antibodies directed against a type I interferon in an individual that is under treatment with said type I interferon, allowing therefore to forecast the unresponsiveness to this treatment. The method is based on the determination of MxA mRNA levels in blood samples that have been incubated in vitro with a suitable amount of a type I interferon. The results obtained by in vitro incubation of blood samples in the presence of a type I interferon permit to evaluate the in vivo condition (responder or non responder) of an individual to a type I IFN treatment.

BACKGROUND

Multiple sclerosis (MS) is a chronic, inflammatory disease that affects the central nervous system (CNS). MS can cause a variety of symptoms, including changes in sensation, visual problems, muscle weakness, depression, difficulties with coordination and speech, severe fatigue, and pain. Although many patients lead full and rewarding lives, MS can cause impaired mobility and disability in more severe cases.

Multiple sclerosis affects neurons, the cells of the brain and spinal cord that carry information, create thought and perception, and allow the brain to control the body. Surrounding and protecting some of these neurons is a fatty layer known as the myelin sheath, which helps neurons carry electrical signals. MS causes gradual destruction of myelin (demyelination) and transection of neuron axons in patches throughout the brain and spinal cord. The name multiple sclerosis refers to the multiple scars (or scleroses) on the myelin sheaths. This scarring causes symptoms which vary widely depending upon which signals are interrupted. It is thought that MS results from attacks by an individual's immune system on the nervous system and is therefore categorized as an autoimmune disease.

MS currently does not have a cure, though several treatments are available which may slow the appearance of new symptoms. Interferon-beta (IFNβ), a type-I Interferon, is a pleiotropic cytokine with immunomodulatory properties and has become a global standard in the treatment of MS. Despite the well documented efficacy in responders to this medication, a substantial number of patients fail to respond to IFNβ. Why IFNβ therapy is or is not effective with respect to MS, and how IFNβ alters the clinical course of MS remains unclear. Putative mechanisms of action include the inhibition of T cell proliferation, regulation of a large number of cytokines, and blocking of blood-brain barrier opening via interference with cell adhesion, migration and matrix metalloproteinase activity.

Furthermore, unfortunately, many multiple sclerosis patients treated with IFNβ develop anti-IFNβ antibodies, which can interfere with the bioactivity of the injected cytokine. These neutralizing antibodies (NAB) prevent IFNβ from binding to its receptor, thereby blocking all the biological effects of IFNβ. This phenomenon is called "antibody-mediated decreased bioactivity (ADB)". The incidence and titers of neutralizing antibodies that develop to IFNβ vary by the preparation of IFNβ used (IFNβ-1b and IFNβ-1a). Other factors that may influence the induction of NAB to IFNβ include the dose, frequency of administration, route of administration and treatment duration.

At present, two major types of assays are used to detect NAB to IFNβs: a) binding assays, which measure the ability of neutralizing antibodies in a patients' sera to bind to IFNβ, and b) neutralization assays (or bioassays), which measure the ability of patients' sera to neutralize the biologic effects of IFNβ.

An example of such neutralizing assay is the myxovirus resistance protein A (MxA) assay. This assay is based on evidence that type 1 IFNs selectively induce the Mx1 gene in human cells in a dose-dependent manner. The assay is based on detection using real-time RT PCR of gene expression of MxA to determine the in vivo biological effect of administered IFNβ. The Mx1 gene is expressed at very low levels before and relatively high levels after IFNβ treatment. The assay consists of taking a blood sample of a patient before and after injection within a few hours of the patient with a dose of IFNβ. Peripheral blood mononuclear cells are then collected and PCR is used to determine the level of MxA mRNA in the sample. When IFNβ binds and activates its receptor, the level of MxA RNA should be substantially increased in the postdose sample compared with the predose sample. If MxA RNA is not induced, this indicates that the injected IFN was unable to activate its receptor.

MxA assays may also be applied to evaluate IFNα bioavailability in patients suffering from hepatitis C (HCV) and/or hepatitis B (HBV) and treated with different IFNα regimes.

However, assays used to detect NAB in general differ in their sensitivity and specificity, and there can be high variability between laboratories in how these assays are performed. In addition, the above-described MxA assay in particular has the drawback that the assay is not patient-friendly. The assay requires the presence of a patient for donating a predose and postdose blood sample.

It is therefore an aim of the present invention to provide an improved method for monitoring the in vivo response of an individual to a treatment with a type I interferon (type I IFN), which overcomes at least some of the above-mentioned drawbacks of known methods.

More in particular, it is an aim of the invention to provide an in vitro method for monitoring the in vivo response of an individual to a treatment with a type I interferon.

The present invention also aims to provide an improved method for monitoring the development and/or occurrence of neutralizing antibodies in the course of a treatment with a type I interferon. More in particular, the present inventions aims to provide an improved in vitro method for evaluating the in vivo presence of antibodies directed against a type I interferon in an individual that is under treatment with said type I interferon.

SUMMARY

The present invention is in general directed to an in vitro method for following-up the therapeutic and/or biologic response of an individual to a treatment with a type I interferon (type I IFN).

The term "response of an individual" as used herein refers to the condition of an individual that is being treated with a type I IFN. Such condition may or may not involve the development and/or occurrence of neutralizing antibodies directed against the type I IFN administered to the individual. Individuals can therefore also be identified as "responders" and "non responders" (see further below).

In a first aspect, the invention relates to an in vitro method for evaluating the in vivo presence of a factor that prevents the biological effect of a type I IFN in an individual that is under treatment with said type I interferon comprising incubating a whole blood sample of said individual in vitro with a suitable amount of said type I interferon for a suitable period of time, and determining mRNA levels of the gene encoding myxovirus resistance protein A (MxA) in said blood sample.

The term "factor" as used herein refers to any substance or condition that prevents the biological effect of IFN. Non-limitative examples of such factors may include mutation of the receptor, soluble receptor, the presence of NABs, etc.

The present invention is in particular directed to a method for determining the responsiveness to type I interferon therapy and more precisely for evaluating the in vivo presence of antibodies directed against a type I IFN in an individual that is under treatment with said type I interferon. The method comprises incubating a whole blood sample of said individual in vitro with a suitable amount of said type I interferon for a suitable period of time, and determining mRNA levels of the gene encoding myxovirus resistance protein A (MxA) in said whole blood sample. MxA protein is also known as the interferon-induced p78 protein. MX1 is the gene encoding the interferon-induced MxA protein. In the present method, blood samples taken from an individual are incubated in vitro with a suitable amount of IFN. In contrast, in vivo methods for evaluating the presence of antibodies directed against a type I IFN in an individual involve the analysis of blood sample(s) of an individual that has been injected with a suitable amount of IFN.

The present method may be applied to any individual suffering from a disease which can be treated with a type I interferon, including for instance multiple sclerosis, chronic hepatitis C (HCV), or chronic hepatitis B (HBV).

The present method is very accurate and rapid. Furthermore, the applicant has shown that there is an excellent correlation between results obtained by the in vitro incubation of blood samples (cells) with a type I IFN and the in vivo response of the patients to the IFN therapy.

Also, constraints for a patient are reduced to a minimum since the present method only requires a single blood sample (predose sample) of the patient. The presence of a patient for donating a postdose blood sample is no longer required, since according to the present method injection of a patient with an amount of IFN is not required anymore for determining the in vivo condition of said patient. In addition, the present method is particularly suitable for being routinely applied.

In another aspect, the invention relates to a kit for evaluating the in vivo presence of antibodies directed against a type I interferon in an individual that is under treatment with said type I interferon.

A kit according to the invention comprises
 a) one or more vessel suitable for accepting a blood sample,
 b) a primer pair specific to the mRNA of the Mx1 gene, and
 c) a probe designed to anneal to an internal region of the produced MxA cDNA,
wherein said vessel comprises: a) a type I interferon present inside said vessel, b) a container in which a stabilizing agent is present, c) a connection between the inside of said vessel and the inside of said container, d) a physical barrier that temporarily blocks said connection.

Another kit according to the invention comprises:
 a primer pair specific to the mRNA of the Mx1 gene, for the transcription of said mRNA of the Mx1 gene into cDNA and the amplification of the latter,
 a probe designed to anneal to an internal region of the produced MxA cDNA,
 a control primer pair specific to the mRNA of a control gene which is suitable for the transcription of mRNA of said control gene into cDNA and the amplification of the latter, and
 a control probe designed to anneal to an internal region of the produced control cDNA.

Those skilled in the art will immediate recognize the many other effects and advantages of the present method and the numerous possibilities for end uses of the present invention from the detailed description and examples provided below.

DETAILED DESCRIPTION OF THE INVENTION

Figure 1:
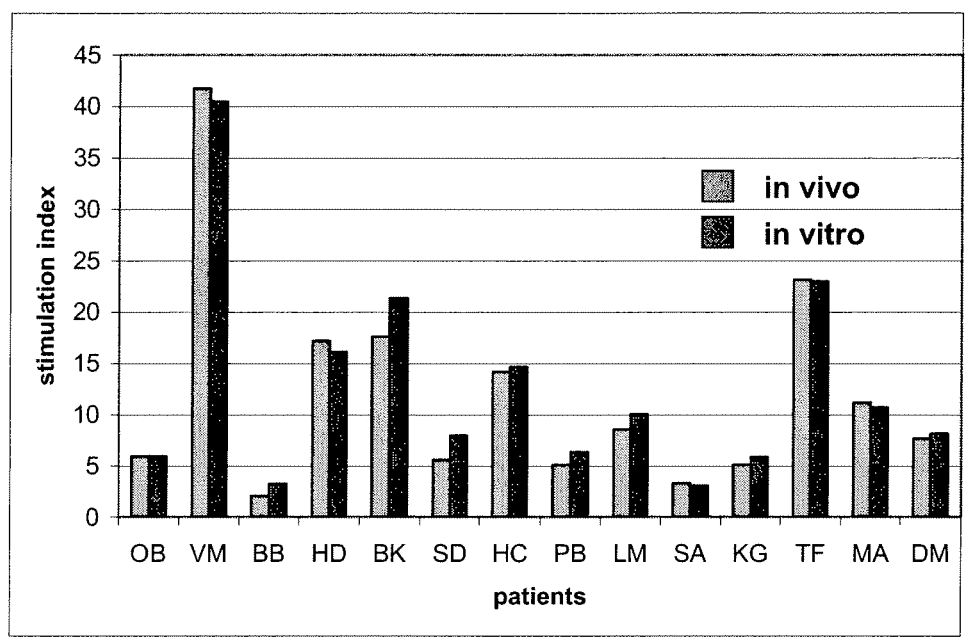
FIG. 1 illustrates the stimulation index, being equal to the MxA mRNA levels after injection (in vivo) or stimulation (in vitro) divided by the MxA mRNA levels before injection or stimulation for several patients. MxA mRNA levels are firstly corrected against RPLP0 mRNA levels. RPLP0 is the Human Acidic Ribosomal Phosphoprotein P0, and is used here as housekeeping (control) gene for normalization. The administered IFNs comprise: IFNβ-1a (Rebif® (BB, SA) or Avonex® (HD, VM, BK, SD, HC, LM, TF, MA and DM)) or IFNβ-1b (Betaferon® (OB, PB and KG)).

Many studies have described the beneficial effects of type I interferon (IFNα and IFNβ) in the treatment of patients suffering from a wide variety of diseases. Interferons (IFNs) are natural proteins produced by the cells of the immune system of most vertebrates in response to challenges by foreign agents such as viruses, bacteria, parasites and tumor cells. Interferons belong to the large class of glycoproteins known as cytokines. IFNs have been used therapeutically in multiple sclerosis (MS), chronic hepatitis C (HCV), chronic hepatitis B (HBV) and certain types of solid and hematological malignancies. However, during such treatment, a gradual loss of clinical response is observed in many patients. For such individuals, it is therefore highly desirable to find appropriate biological markers for monitoring the clinical efficacy of a treatment with type I IFNs.

Binding of IFN to its receptor on the surface of the cellular membrane induces a signal cascade resulting in the activation of transcription factors and synthesis of different proteins, so-called interferon-induced proteins, such as beta2-microglobulin, GTP-cyclohydrolase and Mxproteins. Among these latter proteins, the "human myxovirus resistance protein" type A (MxA) is exclusively induced by type I (alpha and beta) IFN or by certain viruses in a dose dependent manner. In the present invention, use is made of the myxovirus resistance protein A (MxA) as a biological marker for monitoring the clinical efficacy of a treatment with type I IFNs.

In a first aspect, the invention provides a method for evaluating the in vivo presence of antibodies directed against a type I interferon in an individual that is under treatment with said type I interferon comprising incubating a blood sample of said individual in vitro with a suitable amount of said type I interferon for a suitable period of time, and determining mRNA levels of the gene encoding myxovirus resistance protein A (MxA) in said blood sample.

In a particular embodiment, said method comprises incubating in a vessel a blood sample of said individual in vitro with a suitable amount of said type I interferon and mixing the sample with a stabilizing agent. Preferably, said stabilizing agent is contained in a separate compartment in said vessel. The method can further comprise determining mRNA levels of the gene encoding myxovirus resistance protein A (MxA) in said blood sample.

The terms "individual" or "patient" are used herein as synonym and preferably refer to a human suffering from a disease which can be treated with a type I interferon. Such individual may for instance comprise a patient suffering from multiple sclerosis, (chronic) hepatitis C (HCV) and/or B (HBV), etc.

The term "evaluating" as used herein preferably refers to both qualitatively detecting and quantifying.

The terms "stimulation" or "incubation" are used herein as synonyms and refer to the technique of growing a sample of blood in vitro in the presence of a certain amount of an active compound, in particular an type I interferon according to the present invention.

In a preferred embodiment, the type I interferon according to the invention may comprise an IFNβ or an IFNα interferon, depending on the disease which affects the individual to be monitored. In one embodiment, the treatment with a type I interferon involves a treatment of multiple sclerosis with an IFNβ. Preferably, said treatment with an IFNβ comprises a treatment with an IFNβ-1a or an IFNβ-1b. Examples of pharmaceutical preparations comprising IFNβ-1a may comprise Rebif® and Avonex®. Examples of pharmaceutical preparations comprising IFNβ-1 b may comprise Betaferon®.

In another preferred embodiment, the treatment with a type I interferon involves a treatment of chronic hepatitis C (HCV) with an IFNα. Said treatment with an IFNα may comprise a treatment with an IFNα-2a or an IFNα-2b. Examples of pharmaceutical preparations comprising IFNα-2a may comprise Pegasys® and Roferon®. Examples of pharmaceutical preparations comprising IFNα-2b may comprise Intron A® and Pegintron®.

In a preferred embodiment, a suitable amount of IFNβ-1a and IFNβ-1b added to the blood sample may be comprised between 10 and 100 IU/mL, and preferably comprised between 50 and 100 IU/mL to reach the best stimulation index.

The term "blood sample" applied in the present method refers to a "whole blood sample". The term "whole blood" as used herein refers to blood as it is collected by venous sampling, i.e. containing white and red cells, platelets, and plasma. It is noted that it is not possible to perform in vitro incubation on peripheral blood mononuclear cells (PBMC) to detect NAB, because PBMC do not contain antibodies. Antibodies are present in plasma, and therefore in whole blood.

The terms "antibodies directed against a type I IFN" or "neutralizing antibodies" are used herein as synonyms and refers to antibodies that prevent a type I IFN, e.g. IFNα or IFNβ, from binding to its respective receptor, thereby blocking all the biological effects of the type I IFN. There exist at present different techniques for detecting antibodies directed against a type I IFN using MxA as a biological marker, including for instance MxA assays.

MxA protein assays include the incubation of cells in microtiter plates with a certain amount of IFN that has been pre-incubated with serial dilutions of serum samples of a patient. After a certain incubation time (e.g. 12 or 24 hours) the cells are lysed and MxA concentration is determined using a quantitative ELISA for MxA. The lower the amount of neutralizing antibodies, the higher the amount of MxA protein that will be measured. This technique is known to provide be sensitive and specific. However, disadvantages of this technique involve difficulty in obtaining the reagents for MxA ELISA (e.g. anti-MxA antibodies) and the variability inherent to the use of cell lines in the assay.

In order to overcome the above-mentioned problems of MxA protein assays, an assay using MxA mRNA is applied in the present method. Variability due to the use of cell lines can be eliminated and because mRNA has a shorter half-life than the protein, the measurement of a specific transcript offers a better measure of the biological activity of IFN. According to the present method, MxA mRNA levels are determined. The higher the amount of neutralizing antibodies, the lower the amount of MxA mRNA, since the neutralizing antibodies interfere with the binding of the IFN to its receptor and block the signal cascade leading to the expression of Mx proteins. Further advantages of determining MxA mRNA levels and not MxA protein levels in vitro include: 1) the need of lower blood samples, 2) the extracted mRNA can be used to detect any other IFN-inducible gene, using specific oligonucleotides if available, and 3) the present method can be performed using a patient's cells instead of cell lines.

In a preferred embodiment, MxA mRNA levels are determined by real-time quantitative polymerase chain reaction (qc-PCR). As used herein, "Real-time quantitative rt PCR" relates to a method that monitors the degradation of a dual-labeled fluorescent probe in real time concomitant with PCR amplification. Input target RNA levels are correlated with the time (measured in PCR cycles) at which the reporter fluorescent emission increases beyond a threshold level. In example 1, a real-time quantitative polymerase chain reaction (qc-PCR) as can be applied in accordance with the present invention is illustrated.

In another preferred embodiment, the method involves incubating a blood sample in the presence of a type I IFN in an incubator, preferably at a temperature of about 37° C. Preferably, the method is performed in the absence of controlling the air composition during incubation. In accordance with the invention, as incubator an oven can be used that is working under ambient atmospheric conditions, i.e. without any regulation of the amounts of $CO_2$ and $H_2O$ present in the oven. In said oven, the sample is preferably maintained at 37° C.

The in vitro induction can be performed in an incubator or oven at 37° C. A cell culture incubator, wherein atmospheric conditions and the concentration of e.g. $CO_2$ are controlled, is not required for carrying out the incubation step of the present method. The Applicant has shown that results obtained after incubation at 37° C. in a incubator, in the absence of a control of $CO_2$ levels (e.g. at 5%) and/or a water saturated atmosphere, are identical to results obtained after incubation at 37° C. in a cell culture incubator, wherein atmospheric conditions are carefully regulated (see for instance example 3).

In a particularly preferred embodiment, the present method for evaluating the in vivo presence of antibodies directed against a type I interferon in an individual that is under treatment with said type I interferon comprises the steps of:
a) providing a first and a second blood sample of said individual prior to in vivo treatment of said individual with said type I interferon,
b) adding in vitro to said second blood sample a suitable amount of said type I interferon;
c) incubating the sample of step b) in vitro for a suitable period of time;
d) determining MxA mRNA levels in the first blood sample of step a);
e) determining MxA mRNA levels in the incubated blood sample of step c);
f) comparing MxA mRNA levels determined in step d) and e), and
g) evaluating the in vivo presence of antibodies directed against a type I interferon in said individual based on the in vitro results obtained in step f).

In an alternative embodiment, the invention relates to a method comprising the steps of
a) providing blood sample of said individual prior to in vivo treatment of said individual with said type I interferon, and dividing said blood sample in a first and a second portion,
b) adding in vitro to the second portion of said blood sample a suitable amount of said type I interferon;
c) incubating the sample of step b) in vitro for a suitable period of time;
d) determining MxA mRNA levels in the first portion of the blood sample of step a);
e) determining MxA mRNA levels in the incubated blood sample of step c);
f) comparing MxA mRNA levels determined in step d) and e), and
g) evaluating the in vivo presence of antibodies directed against a type I interferon in said individual based on the in vitro results obtained in step f).

In another embodiment, the method comprises the steps of:
a) providing a first and a second blood sample of said individual prior to in vivo treatment of said individual with said type I interferon,
b) adding in vitro to said second blood sample a suitable amount of said type I interferon;
c) incubating the sample of step a) and step b) in vitro for a suitable period of time;
d) determining MxA mRNA levels in the incubated first blood sample of step c);
e) determining MxA mRNA levels in the incubated second blood sample of step c);
f) comparing MxA mRNA levels determined in step d) and e), and
g) evaluating the in vivo presence of antibodies directed against a type I interferon in said individual based on the in vitro results obtained in step f).

In an alternative embodiment, the method comprises the steps of
a) providing a blood sample of said individual prior to in vivo treatment of said individual with said type I interferon, and dividing said blood sample in a first and a second portion,
b) adding in vitro to said second portion of said blood sample a suitable amount of said type I interferon;
c) incubating the first portion of said blood sample of step a) and the second portion of said blood sample of step b) in vitro for a suitable period of time;
d) determining MxA mRNA levels in the incubated first portion of said blood sample of step c);
e) determining MxA mRNA levels in the incubated second portion of said blood sample of step c);
f) comparing MxA mRNA levels determined in step d) and e), and
g) evaluating the in vivo presence of antibodies directed against a type I interferon in said individual based on the in vitro results obtained in step f).

The present method thus comprises obtaining one or two blood samples from an individual before the individual is treated with the type I IFN. One blood sample or a part of the blood samples is not further treated and analyzed as such. The second blood sample or the other part of the blood sample is incubated and stimulated in vitro with a suitable amount of a type I IFN during a suitable period of time which may vary from 4 to 12 hours, depending on the IFN that is added to the blood; and which for instance may be about 4, 5, 6, 7 or 8 hours for IFNβ-1a; 4, 5, 6, 7, 8, 9, 10, 11, 12 hours for IFNβ-1b. The method of the present invention provides results much faster than prior art methods, since the blood samples are taken once and incubated with the interferon, while in the prior art in vivo method the second sample of blood is generally collected at least 12 hours after the injection of IFN.

In a preferred embodiment, after incubation and before mRNA determination, the samples are treated with a stabilizing agent. In an embodiment, the stabilizing agent is an inhibitor of cellular RNA degradation and/or gene induction. For example, said inhibitor of cellular RNA degradation and/or gene induction is that as found in a PAXGENE™ Blood RNA Tube. For example, a quaternary amine surfactant may be used as a stabilizing agent. Suitable quaternary amine surfactants, able to stabilize RNA from biological samples, are described in U.S. Pat. No. 5,985,572, WO94/18156 and WO02/00599. One example of a quaternary amine which can be used in the method of the present invention is tetradecyltrimethyl-ammonium oxalate. (U.S. Pat. No. 5,985,572). Alternatively, said cationic detergent may be CATRIMOX-14™ (U.S. Pat. No. 5,010,183) a 0.1 M aqueous solution of tetradecyltrimethylammonmm oxalate.

In an embodiment, the method of the present invention may use a vessel comprising a type I interferon and a container in which a stabilizing agent is present. Preferably, the inside of said vessel and the inside of said container are connected, and a physical barrier temporarily blocks said connection.

The method of the invention can comprise the steps of:
a) providing a first and a second blood sample (or a first and second portion of a blood sample) of an individual under treatment with a type I interferon,
b) adding said second blood sample (or said second blood portion) in a vessel comprising: (i) a suitable amount of type I interferon present inside said vessel, (ii) a container in which a stabilizing agent is present, (iii) a connection between the inside of said vessel and the inside of said container, and (iv) a physical barrier that temporarily blocks said connection.
c) incubating said second blood sample (or second blood portion) in vitro for a suitable period of time;
d) adding to said second blood sample (or second blood portion) the stabilizing agent by removing said physical barrier,
e) determining MxA mRNA levels in said incubated and stabilized blood sample (or second blood portion);
f) adding to said first blood sample (or first blood portion) a stabilizing agent and determining MxA mRNA levels in a said first blood sample (or first blood portion) from said patient,
g) comparing MxA mRNA levels determined in step e) and f), and
h) evaluating the in vivo presence of antibodies directed against a type I interferon in said individual based on the in vitro results obtained in step g).
i) adding to said first blood sample (or first blood portion) the stabilizing agent.

In an embodiment, said first blood sample (or first blood portion) is also incubated, similarly to said second sample (or blood portion), in a vessel as described above but free of type I interferon. This first blood sample is also stabilized with stabilizing agent, as fast as possible after blood collection, or alternatively, after incubation as done for the tube containing IFN.

The method comprises the determination of MxA mRNA levels in the first blood sample of said individual prior to treatment and in the second blood sample that has been incubated with type I IFN. The mRNA level of MxA is compared in both samples and based on the results thereof, the in vivo presence of antibodies directed against a type I interferon in said individual is evaluated.

Absence or presence of such antibodies provides an indication of the condition or response of the patient to a treatment with a type I IFN. Dependent on their response, an individual can therefore also be identified as "responders" and "non responders".

"responders" are defined herein as patients undergoing an IFN treatment and showing a good clinical response to this treatment. In such patient the development or occurrence antibodies directed against a type I interferon is either absent or the amounts of antibodies are present in insufficient amounts to block the biological effects of the IFN.

"Non responders" are defined herein as patients undergoing an IFN treatment and clinically resistant to this treatment because of the development or occurrence in these patients of significant amounts of antibodies directed against a type I interferon in an individual that block the biological effects of the IFN.

In a further embodiment, the method comprises the step of calculating a stimulation index, corresponding to the MxA mRNA levels after in vitro stimulation divided by the MxA mRNA levels before stimulation.

In another embodiment, the present invention therefore also provides a method for monitoring the in vivo response of an individual to a treatment with a type I interferon, comprising incubating a blood sample of said individual in vitro with a suitable amount of said type I interferon for a suitable period of time, and determining mRNA levels of the gene encoding myxovirus resistance protein A (MxA) in said blood sample. The method can be applied using the steps, conditions, amounts and examples of preferred type I IFN and incubation times and conditions or as described above.

In yet another embodiment the invention also provides a method for identifying an individual as a responder or non responder to a treatment with a type I interferon, comprising incubating a blood sample of said individual in vitro with a suitable amount of said type I interferon for a suitable period of time, and determining mRNA levels of the gene encoding myxovirus resistance protein A (MxA) in said blood sample. The method can be applied using the steps, conditions, amounts and examples of preferred type I IFN and incubation times and conditions or as described above.

The invention further provides a method for the in vitro induction of MxA mRNA expression by a type I interferon in mammalian whole blood. The method comprises incubating said whole blood in the presence of a suitable amount of type I IFN for a suitable period of time. Suitable amounts and examples of preferred type I IFN and incubation times and conditions are similar as those given above.

The invention further provides a method for adjusting an IFN-therapy in a patient, comprising the step of identifying an individual as a responder or non responder to a treatment with a type I interferon using the method of the present invention, and adjusting said IFN-therapy when the patient is a non-responder. In an embodiment, said adjusting step comprises discontinuing the therapy. In another embodiment, said adjusting step comprises using a less immunogenic IFN or glatiramer acetate. Preferably, the identification step is performed at least twice before adjusting said IFN-therapy. Preferably, the at least two successive identification steps are separated by 3 to 6 months. The method can be applied using the steps, conditions, amounts and examples of preferred type I IFN and incubation times and conditions or as described above.

Also provided are kits for use in practicing the subject methods. The term "kit" as used herein refers to any combination of reagents or apparatus that can be used to perform a method of the invention.

In one embodiment, the present invention provides a kit for evaluating the in vivo presence of antibodies directed against a type I interferon (IFN) in an individual that is under treatment with said type I interferon, said kit comprising: a suitable amount of a type I interferon, preferably an IFNβ or an IFNα, and a primer pair specific to the mRNA of the Mx1 gene, for the transcription of said mRNA of the Mx1 gene into cDNA and the amplification of the latter and a probe designed to anneal to an internal region of the produced MxA cDNA, and optionally a stabilizing agent.

In a particular embodiment, the kit comprises one or more vessel suitable for accepting a blood sample, said vessel comprising: a) a type I interferon present inside said vessel, b) a container in which a stabilizing agent is present, c) a connection between the inside of said vessel and the inside of said container, d) a physical barrier that temporarily blocks said connection. In another particular embodiment, the kit also comprises one or more vessel suitable for accepting a control blood sample which will not be treated with a type I interferon, said vessel comprising: a container in which a stabilizing agent is present, a connection between the inside of said vessel and the inside of said container, and a physical barrier that temporarily blocks said connection.

In use, the physical barrier of item d) may be opened by the application of physical force to said vessel. Said force may transmit an opening means to said physical barrier. Examples of such physical barriers include rotary valve, aperture valve, slit valve, diaphragm valve, ball valve, flap valve. Alternatively, said force may irreversibly open said physical barrier. Other examples of such physical barriers include a plug which is forced out of position, a barrier which shatters upon the application of force. In an embodiment, the inside of said container and the inside of said vessel are connected, and the flow of stabilizing agent from the container to the vessel is prevented by the surface tension of the stabilizing agent in combination with the aperture size of the connection. According to this aspect, at an appropriate time an application of force which transmits to the stabilizing agent, forces the stabilizing agent from the container into the vessel. The force may be applied, for example, by squeezing, continually inverting, and agitating.

The type I interferon can be provided in said vessel in a liquid or lyophilized form, not immobilized. The type I interferon can also be immobilized on part or all of the inside surface of said vessel. The inside wall of the vessel may be lined with a suitable coating enabling the type I interferon to be attached. In another embodiment, said type I interferon is immobilized on a solid support. The solid support may be attached to the inside of the vessel. Alternatively, the solid support may be free of the inside of the vessel. Examples of solid supports include, but are not limited to, chromatography matrix, magnetic beads.

The vessel may be sealed with resealing means such as a screw-cap, push-on cap, a flip-cap. Said vessel may comprise one or more openings. In a particular embodiment, the vessel as described above comprises one or more areas suitable for puncture by a syringe needle, such as a re-sealable septum. The vessel may comprise a fitting suitable for receiving a syringe or a syringe needle and transmitting the contents therein to the interior of said vessel. Suitable vessel may further comprise cannular suitable for withdrawing bodily fluids.

Suitable vessel may further comprise a valve which is capable of minimizing the flow of gas/liquid from vessel, and allowing the flow of biological sample into the vessel. Suitable vessel may further comprise a means through which displaced gas may be expelled. Said means are known the art and include valves, non-drip holes, vents, clothed-vents, expandable vessel walls, use of negative pressure within said vessel. Said vessel may further be held under negative pressure. The negative pressure may be utilized to relieve the pressure build-up upon introduction of whole blood into said sealed vessel. Alternatively, or in addition, the negative pressure may be at a predetermined level and may be utilized so as to allow the introduction of a fixed volume of whole blood. Suitable vessel may comprise an indication for dispensing a known volume of stabilizing agent therein.

In an embodiment, the stabilizing agent is an inhibitor of cellular RNA degradation and/or gene induction. For example, said inhibitor of cellular RNA degradation and/or gene induction is that as found in a PAXGENE™ Blood RNA Tube with RNA preservative solution. For example, a quaternary amine surfactant may be used as a stabilizing agent. Suitable quaternary amine surfactants, able to stabilize RNA from biological samples, are described in U.S. Pat. No. 5,985,572, WO94/18156 and WO02/00599. One example of a quaternary amine which can be used in the method and kits of the present invention is tetradecyltrimethyl-ammonium oxalate. (U.S. Pat. No. 5,985,572). Alternatively, said cationic detergent may be CATRIMOX-14™ (U.S. Pat. No. 5,010,183) a 0.1 M aqueous solution of tetradecyltrimethylammonmm oxalate.

In a preferred embodiment, the kit comprises one or more vessel suitable for accepting a blood sample, a primer pair specific to the mRNA of the Mx1 gene, a probe designed to anneal to an internal region of the produced MxA cDNA, wherein said vessel comprises: a) a type I interferon present inside said vessel, b) a container in which a stabilizing agent is present, c) a connection between the inside of said vessel and the inside of said container, d) a physical barrier that temporarily blocks said connection. In an embodiment, said kit further comprises a control primer pair specific to the mRNA of a control gene, and a control probe designed to anneal to an internal region of the produced control cDNA. In another particular embodiment, the kit also comprises one or more vessel suitable for accepting a control blood sample which will not be treated with a type I interferon, said vessel comprising: a container in which a stabilizing agent is present, a connection between the inside of said vessel and the inside of said container, and a physical barrier that temporarily blocks said connection.

In one embodiment, the present invention provides a kit for evaluating the in vivo presence of antibodies directed against a type I interferon (IFN) in an individual that is under treatment with said type I interferon comprising: a primer pair specific to the mRNA of the Mx1 gene, a probe designed to anneal to an internal region of the produced MxA cDNA, a control primer pair specific to the mRNA of a control gene, and a control probe designed to anneal to an internal region of the produced control cDNA. The kit may further comprise means for performing PCR reactions, preferably qc-PCR reactions. The kit may further comprise media and solution suitable for taking a blood sample and for extracting mRNA from said blood sample. The kit may further comprise a suitable amount of a type I interferon, preferably an IFNβ or an IFNα. In an embodiment, said type I interferon is provided in a vessel comprising a container with a stabilizing agent. Suitable vessels comprising a type I interferon and a container with a stabilizing agent are described above. Preferably said kits comprise amount of IFNβ-1a or of IFNβ-1b that is comprised between 10 and 100 IU/mL. Preferably, the primer pair specific to the mRNA of the Mx1 gene comprises oligonucleotide sequences represented by SEQ ID NO: 1 and SEQ ID NO: 2. Preferably, the probe designed to anneal to an internal region of the produced comprises an oligonucleotide sequence represented by SEQ ID NO: 3.

In an embodiment, said control gene is selected from the group comprising mRNAs for certain ribosomal proteins such as RPLP0 (ribosomal protein, large, P0), glyceraldehyde-3-phosphate dehydrogenase mRNA, beta actin mRNA, MHC I (major histocompatibility complex I) mRNA, cyclophilin mRNA, 28S or 18S rRNAs (ribosomal RNAs). In a preferred embodiment, said control gene is the Human Acidic Ribosomal Phosphoprotein P0 (RPLP0 gene). In a preferred embodiment, said primer pair specific to the mRNA of said control gene comprises oligonucleotide sequences represented by SEQ ID NO: 4 and SEQ ID NO: 5 or represented by SEQ ID NO: 7 and SEQ ID NO: 8. Preferably the probe designed to anneal to an internal region of the produced control cDNA, comprises an oligonucleotide sequence represented by SEQ ID NO: 6 or by SEQ ID NO: 9.

The kit can further comprise additional components for carrying out the method of the invention, such as RNA extraction solutions, purification column and buffers and the like. The kit of the invention can further include any additional reagents, reporter molecules, buffers, excipients, containers and/or devices as required described herein or known in the art, to practice a method of the invention.

The various components of the kit may be present in separate containers or certain compatible components may be pre-combined into a single container, as desired. In addition to the above components, the kits may further include instructions for practicing the present invention. These instructions may be present in the kits in a variety of forms, one or more of which may be present in the kit.

One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Any convenient means may be present in the kits.

The following examples are intended to illustrate and to substantiate the present invention.

EXAMPLES

Example 1

In vitro Whole Blood Stimulation: Methodology for mRNA Extraction and Real Time PCR In vitro whole blood stimulation is performed on heparinized venous blood with or without the concerned IFN at 37° C. mRNA extraction and real time PCR is carried out as previously described (1, 2). Briefly, stimulation is stopped by adding the reagent contained in PAXGENE™ tubes, an RNA preservative solution (Qiagen, Westburg, The Netherlands). This reagent induced total cell lysis and mRNA stabilization by nucleic acids precipitation. The nucleic acids pellet is then dissolved in the lysis buffer contained in the MagNA Pure™ mRNA extraction kit (Roche Applied Science, Roche Diagnostics Belgium, Vilvoorde, Belgium). mRNA is extracted from 300 µl of this solution, using this kit on the MagNA Pure™ instrument (Roche Applied Science) following manufacturer's instructions ("mRNA I cells" Roche's protocol). Reverse transcription and real-time PCR are performed in one step on a LightCycler instrument, following the standard procedure described in the "LightCycler—RNA Master Hybridization Probes" Kit (Roche Applied Science).

Oligonucleotides sequence and final concentration for the MxA mRNA are as follows: ACACGAGTTCCACAAATG-GAGTA (SEQ ID NO: 1) at 300 nM for the forward primer, CGATTGTCTCAAATGTCCTGTAA (SEQ ID NO: 2) at 300 nM for the reverse primer, and TCGTGGTAGAGAGCT-GCCAGGCTTT (SEQ ID NO: 3) at 300 nM for the probe. After an incubation period of 20 minutes at 61° C. to allow mRNA reverse transcription, and then an initial denaturation step at 95° C. for 30 s, temperature cycling is initiated. Each cycle consists of 95° C. for 0 (zero) second and 60° C. for 20 s, the fluorescence being read at the end of this second step. 45 cycles are performed, in total. For each sample, the mRNA copy number is calculated from a standard curve. This latter is constructed for each PCR run from serial dilutions of a purified DNA. mRNA levels are expressed in absolute copy numbers normalized against house keeping gene mRNA (MxA mRNA copies per million of reference gene mRNA copies). RPLP0

(Human Acidic Ribosomal Phosphoprotein P0) was used as house keeping gene, with the following oligonucleotide sequence and final concentration: TGTCTGTCTGCAGAT-TGGCTAC (SEQ ID NO: 4) at 300 nM for the forward primer, AGATGGATCAGCCAAGAAGG (SEQ ID NO: 5) at 600 nM for the reverse primer, and CGGATTACACCTTC-CCACTTGCTGA (SEQ ID NO: 6) at 300 nM for the probe, or alternatively, CCTTTGGGCTGGTCAT (SEQ ID NO: 7) at 300 nM for the forward primer, GCACTTCAGGGTTG-TAG (SEQ ID NO: 8) at 900 nM for the reverse primer, and CCAGCAGGTGTTCGACAATGGC (SEQ ID NO: 9) at 300 nM for the probe.

The complete procedure including whole blood incubation in vitro for 4 hours can be performed in 8 hours or less.

Figure 4:
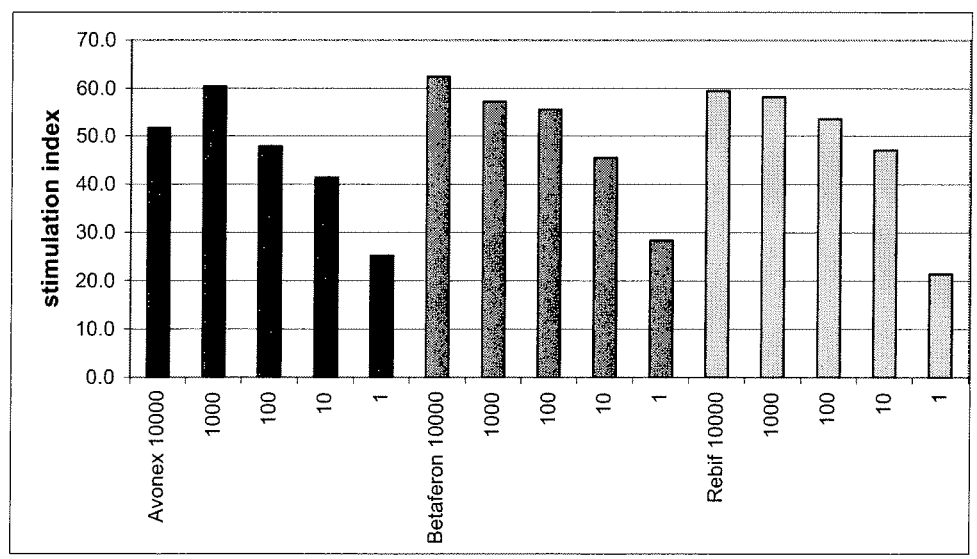
FIG. 4 illustrates the results obtained when incubating a whole blood sample from a healthy subject for four hours in increasing concentrations (1 to 10,000 IU/mL) of Avonex®, Betaferon® or Rebif®.

FIG. 4 illustrates the results obtained when incubating a whole blood sample from a healthy subject for four hours in increasing concentrations (1 to 10,000 IU/mL) of Avonex®, Betaferon® or Rebif. The stimulation index corresponds to the MxA mRNA levels after in vitro stimulation divided by the MxA mRNA levels before stimulation. A plateau is reached between 100 to 1,000 IU/mL. Induction of MxA mRNA by IFNβ may reach a plateau between 100 to 1,000 IU/mL of IFNβ.

Example 2

Comparing the Determination of MxA mRNA Levels by an In vitro Method According to the Invention with the Determination of MxA mRNA Levels Using an In vivo Known in the Prior Art The present experiment compares a) the biological response obtained in vivo after injections of IFNβ in patients with MS with b) the in vitro response of whole blood from the same patients after stimulation of the blood in vitro with IFNβ. In this experiment, MxA mRNA levels were determined on whole blood using RT-PCR quantification.

According to the present method, MxA mRNA is quantified by real time PCR using 200 µl of whole blood incubated in vitro in the present of an IFN (with which the patient is generally treated). In this manner, it is not necessary to take at a precise time post injection a blood sample from the patient. In order to validate this approach, the levels of MxA mRNA obtained after a certain incubation time in vitro were compared with the levels of MxA mRNA in a patient's blood circulating for a same lapse of time after injection of the patient.

General Methodology:

In vivo method: one blood sample was collected prior to injection of a patient with IFNβ. Then four hours after IFNβ injection of the patient, a second blood sample was collected from the patient. MxA mRNA levels were quantified on whole blood in vivo before and after IFNβ injection.

In vitro method: one blood sample was collected from a patient prior to injecting this patient with IFNβ. To about 200 µL of blood sample IFNβ (with which the patient is generally treated) was added in vitro and the blood sample was stimulated (incubated) for four hours. MxA mRNA levels were quantified on whole blood in vitro before and after blood stimulation by 100 IU/mL of IFNβ.

RT-qPCR: mRNA extraction and real time PCR were carried out as described under example 1. Briefly, mRNA was stabilized using the reagent contained in the PAXGENE™ tubes, an RNA preservative solution, (Qiagen Benelux, Venlo, the Netherlands) immediately at the time of blood sample collection for the in vivo analysis and after incubation for the in vitro analysis. mRNA extraction was performed on the MagNA Pure (Roche Applied Science, Vilvoorde, Belgium). A co-amplification of MxA mRNA and RPLP0 (as control) were then performed on a Lightcycler (Roche Applied Science) by using Taqman probes.

In vivo injection of IFN: the day of the experiment, administered IFNs comprised: IFNβ-1a (Rebif® 44 µg subcutaneously) (FIG. 1, BB, SA) or Avonex® (30 µg intramuscularly) (FIG. 1, HD, VM, BK, SD, HC, LM, TF, MA and DM) or IFNβ-1b (Betaferon® 62.5 µg (FIG. 1, OB) or 250 µg (FIG. 1, PB and KG) subcutaneously).

In vitro stimulation of whole blood with 100 IU/mL Rebif® (FIG. 1, BB, SA), 100 IU/mL Avonex® (FIG. 1, HD, VM, BK, SD, HC, LM, TF, MA and DM) or Betaferon® 25 IU/mL (FIG. 1, OB) or 100 IU/mL (FIG. 1, PB and KG).

MxA mRNA levels after stimulation/injection with IFNβ were quantified using the above-referred RT-qPCR technique.

A stimulation index=the MxA mRNA levels after injection (in vivo) or stimulation (in vitro) divided by the MxA mRNA levels before injection or stimulation was calculated. FIG. 1 illustrates the stimulation index for several patients. In FIG. 1, OB refers to a first injection of Betaferon®, which is therefore administrated at a quarter of dose, i.e. 62.5 µg. Hence, for in vitro stimulation, Betaferon® has been added at 25 IU/mL for this patient, instead of 100 IU/mL. DM refers to a first injection of Avonex®; BB and SA refer to patients being in treatment of Rebif® for more than one year and clinically resistant to the treatment (more than 3 exacerbations during the last year); VM, HD, BK, SD, HC, TF and MA refer to patients being in treatment of Avonex® for more than one year and showing a good clinical response to the treatment. PB and KG refer to patients being in treatment of Betaferon® for more than one year and showing a good clinical response to the treatment. LM refers to a patient being in treatment of Avonex® for 82 days and who seems to show a good clinical response to the treatment.

Figure 2:
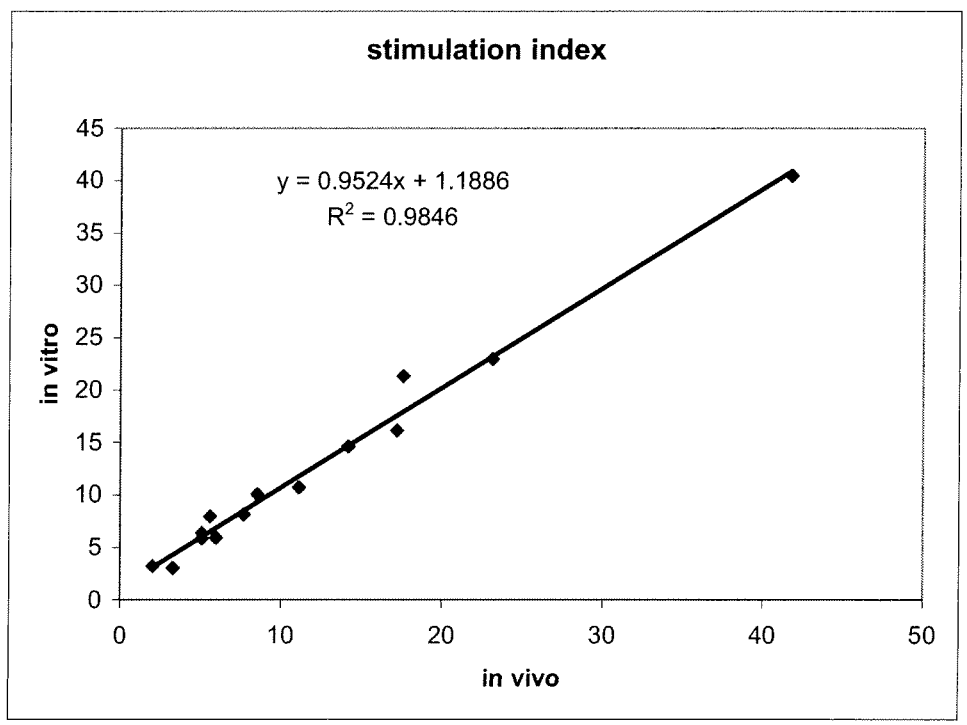
FIG. 2 illustrates the correlation between results obtained using the in vitro method according to an embodiment of the present invention and an in vivo method of the prior art.

From FIG. 1 it can be concluded that there is an excellent correlation between the results obtained with the in vivo method and those obtained with the in vitro method. This can also be seen in FIG. 2, illustrating the correlation ($R^2$=0.9846) between in vivo and in vitro data. The present in vitro method is precise and reliable for a physician and less constraining for patients compared to currently available methods. It can be used as a routine technique for assessing the biological activity of IFNβ.

In addition, FIG. 1 also illustrates that the higher the stimulation index, and thus the levels of MxA mRNA after injection of the patient or stimulation of the blood, the better the response of the patient on the IFN treatment, and the lower the amount of neutralizing antibodies present in the patient. The lowest stimulation indexes are observed for the two patients who are resistant to the treatment, i.e. BB and SA. A low stimulation index is also observed for OB who received a first dose of Betaferon®, but this dose was the quarter of the usual dose (this is generally the case for the first dose, in order to prevent much important side-effects). The higher stimulation index is observed for VM. Interestingly, this patient presented very important side-effects when he received its first injection, suggesting a high responsiveness to IFNβ.

Figure 5:
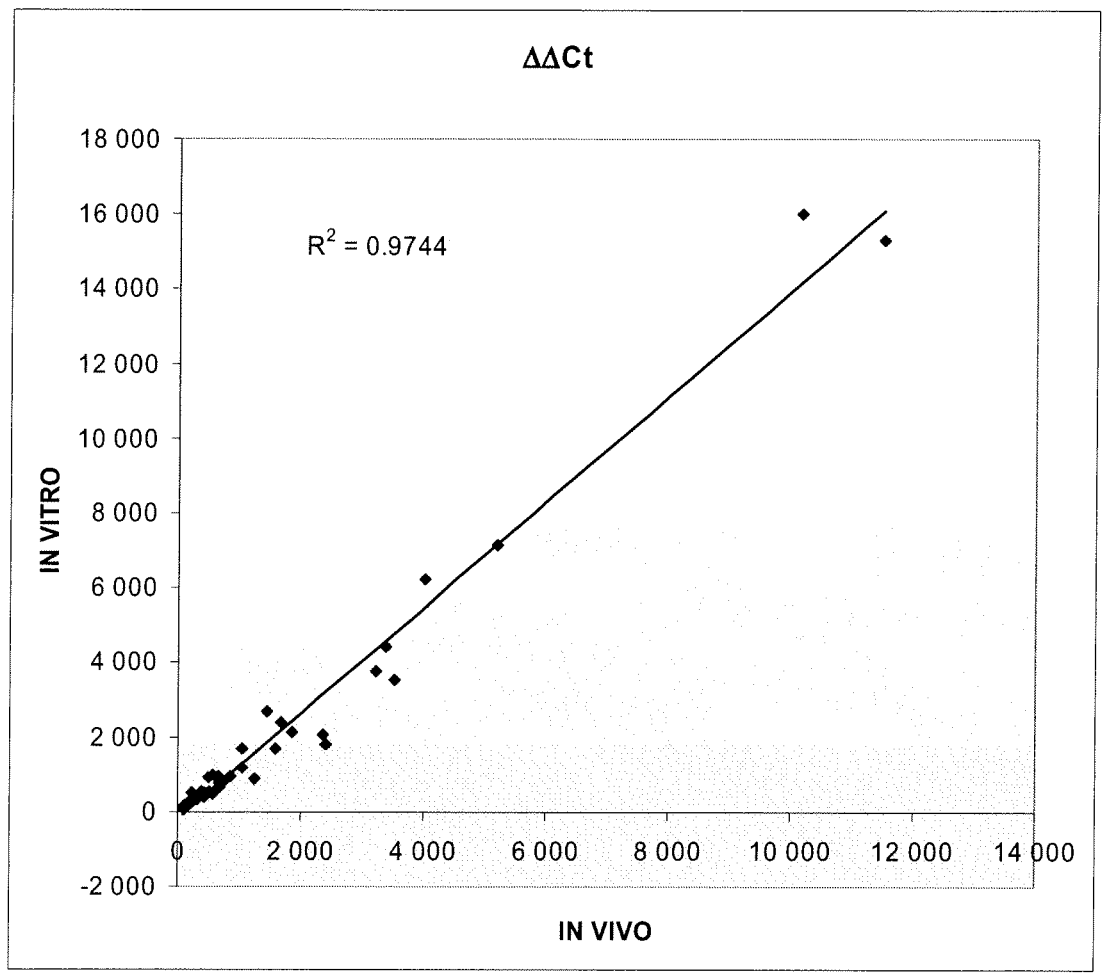
FIG. 5 illustrates the correlation between the results obtained using the in vitro method according to an embodiment of the present invention and an in vivo method of the prior art. Results are expressed using the ΔΔCt method, the conditions "non-stimulated" or "before injection" being used as the reference samples, respectively in the in vitro or in the in vivo method, while RPLP0 mRNA was used as the calibrator, the target being MxA mRNA.

FIG. 5 shows the correlation between results obtained using the in vitro method according to the present invention and an in vivo method of the prior art. 37 patients are included. Results are expressed in ΔΔCt: non-stimulated blood (in vitro test) or blood before injection of IFN (in vivo test) are considered as the reference sample, RPLP0 the calibrator mRNA and MxA the target mRNA, both being amplified together in one reaction tube with similar efficiency. In FIG. 5: A, B and R stand for Avonex®, Betaferon® and Rebif®, respectively.

Figure 6:
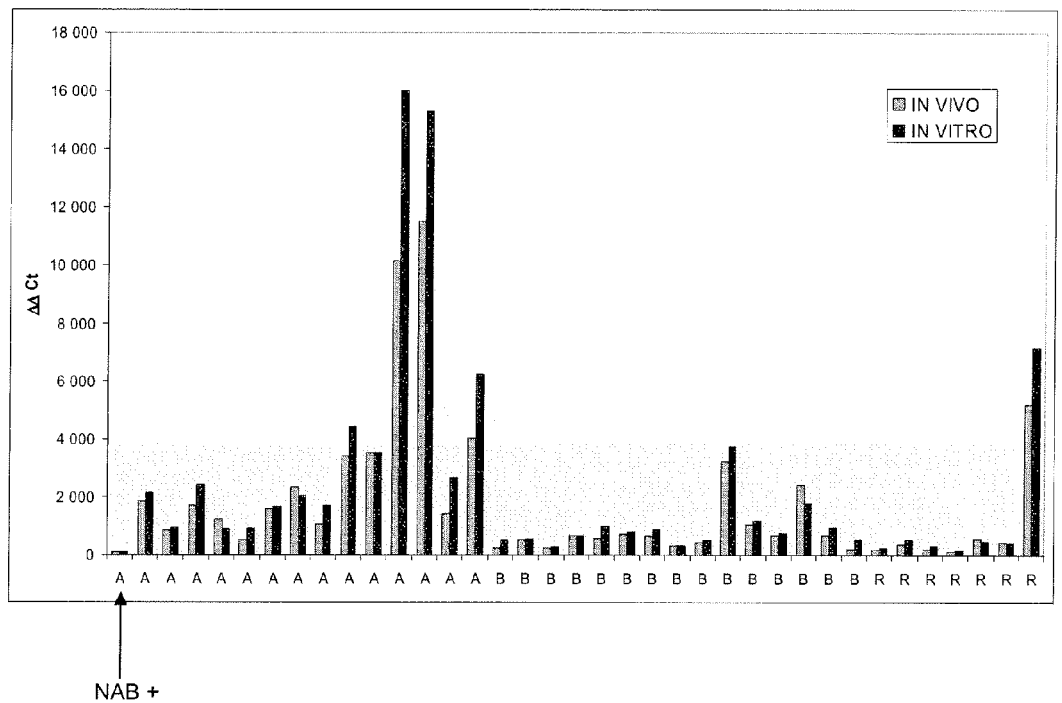
FIG. 6 illustrates the results obtained for 37 patients suffering from multiple sclerosis, using the in vitro method according to an embodiment of the present invention and the in vivo method of the prior art. Results are expressed using the ΔΔCt method, like in FIG. 5. A, B and R stand for Avonex®, Betaferon® and Rebif®, respectively. A patient known to have high titer of NAB is indicated.

FIG. 6 illustrates the results obtained for both tests (the in vitro method according to an embodiment of the present invention and an in vivo method of the prior art) with 37 patients receiving Avonex®, Betaferon® or Rebif® immunotherapy (respectively A, B and R on the X-axis). The results are expressed in ΔΔCt: non-stimulated blood (in vitro test) or blood before injection of IFN (in vivo test) are considered as the reference sample, RPLP0 the calibrator mRNA and MxA the target mRNA, both being amplified together in one reaction tube with similar efficiency. The patient known to have high titer of neutralizing antibodies (NAB) is indicated. He gave the lowest ΔΔCt.

Figure 7:
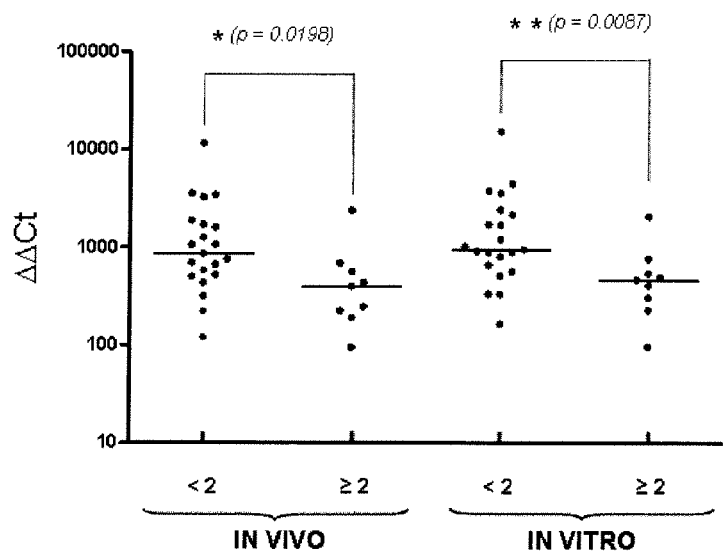
FIG. 7 illustrates the clinical value of MxA mRNA levels determined using an in vitro method according to an embodiment of the invention and an in vivo method known in the prior art. Patients suffering from multiple sclerosis were classified in two groups: those who presented an active disease, defined as two relapses or more (≧2) over the last year, and those considered in a remitting phase (less than two relapses over the last year (<2). Patients presenting an active disease showed lower MxA mRNA levels than those in a remitting phase. A significant statistical difference was found between the two groups of patients, with a higher statistical significance for the in vitro test. The p value has been calculated using a Mann-Whitney test. Results are expressed using the ΔΔCt method, like in FIG. 5.

FIG. 7 compares the clinical values of MxA mRNA levels determined using an in vitro method according to an embodiment of the invention and an in vivo method known in the prior art. MxA mRNA levels were correlated to the clinic. The p value has been calculated using the Mann-Whitney test. Results are expressed in ΔΔCt: Patients suffering from multiple sclerosis were classified in two groups: those who presented an active disease, defined as two relapses or more ($\geq$2) over the last year, and those considered in a remitting phase (less than two relapses over the last year (<2). The patients who presented an active disease, defined as two relapses or more ($\geq$2) over the last year, showed lower MxA mRNA levels than the patients considered in a remitting phase (less than two relapses over the last year (<2)). A significant statistical difference was found between the two populations of patients, with a higher significance for the in vitro test (the in vitro method according to the present invention) compared to the in vivo test (an in vivo method of the prior art): p value=0.0087 for the in vitro method compared to 0.0198 for the in vivo method.

Example 3

Figure 3:
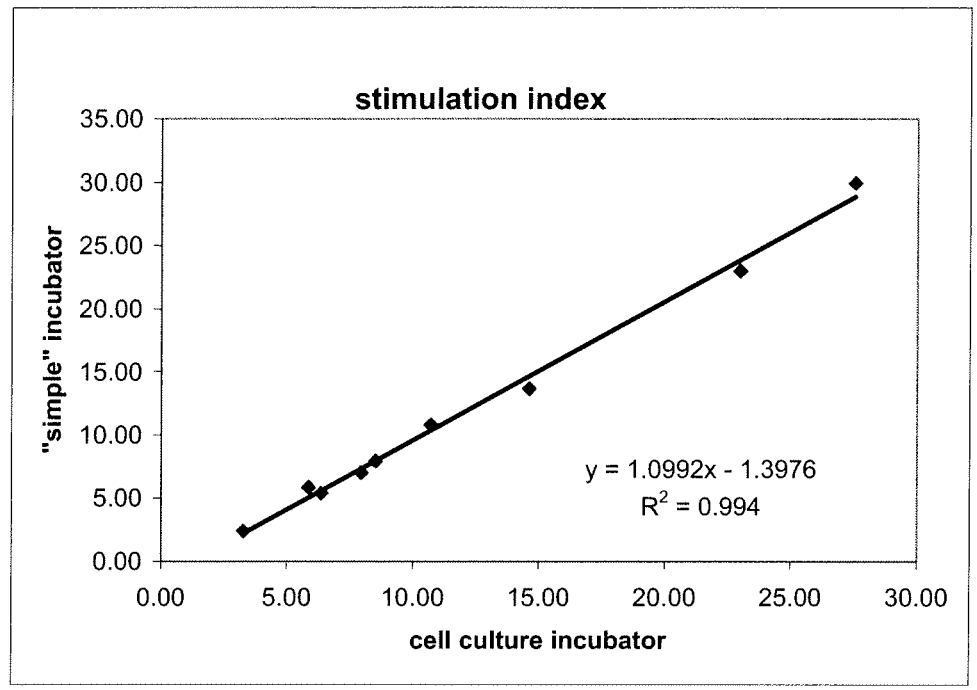
FIG. 3 illustrates the results obtained when incubating a blood sample in a bacterial incubator and in a cell culture incubator.

Incubation of Blood Samples in a "Bacterial" Incubator and in a Cell Culture Incubator The procedure is the same than that described above for in vitro stimulation (same patients, same IFN concentrations . . . ). In this example, blood samples were obtained from eight of the patients presented in example 1 (SA, KG, PB, SD, LM, MA, HC, TF) and an additional patient receiving its first dose of Avonex® (PN). The blood samples were incubated for 4 hours with or without a type I IFN that is administered to the patient. The stimulation index was calculated as: MxA mRNA levels in IFN-stimulated blood samples/MxA mRNA levels in non-stimulated blood samples. Results obtained when incubating the blood samples in a "bacterial" incubator at 37° C. were compared with results obtained when incubating the blood samples in a cell culture incubator, as described in example 1. FIG. 3 illustrates that results obtained after incubation at 37° C. in a simple bacterial incubator, are identical to results obtained after incubation at 37° C. in a cell culture incubator ($R^2$=0.9940).

Application of the Invention

The present method permits to compare a response of a patient to a treatment in vivo using a response obtained in vitro after stimulation (incubation) of whole blood with IFNβ. The present method permits to develop a test which can be routinely used and which involves the measurement and the follow-up of a biological marker for IFN activity. In practical clinical circumstances, such test enables to identify patients that do not respond (or of which the response is reduced) (so-called non responders) to an IFN treatment, and to obtain a direct measurement of the physiological impact of IFN-neutralizing antibodies. The present invention may also find application in a method to adjust the IFN-therapy in non responders based on the results obtained with the monitoring method. The present invention also has numerous applications in clinical and fundamental research.

References

1) Stordeur et al, 2002; J. Immunol. Methods 259:55-64+262: 229 (erratum);
2) Stordeur et al, 2003; J. Immunol. Methods 276:69-77.

What is claimed is:

1. A method for evaluating the in vivo presence of a factor that prevents the biological effect of an IFN-β in an individual that is under treatment of multiple sclerosis with said IFN-β comprising:
   obtaining a first and second whole blood sample from said individual prior to a subsequent administration of IFN-β to said individual,
   incubating the first whole blood sample of said individual in vitro in the presence of a suitable amount of said IFN-β for a suitable period of time,
   performing PCR to determine mRNA levels of the type I IFN-inducible gene encoding myxovirus resistance protein A (MxA) in said first whole blood sample, wherein said factor comprises antibodies directed against an IFN-β, and wherein said MxA mRNA level is compared to that of the second whole blood sample of the same individual incubated for the same period of time in the absence of IFN-β; and
   evaluating the in vivo presence of antibodies directed against an IFN-β in said individual based upon comparison of the first whole blood sample with the second whole blood sample.

2. The method according to claim 1, wherein said treatment with an IFN-β comprises a treatment with an IFN-β-1a or an IFN-β-1b.

3. The method according to claim 1, wherein MxA mRNA levels are determined by real-time quantitative polymerase chain reaction (qc-PCR).

4. The method according to claim 1, wherein said blood sample is incubated with an amount of IFNβ-1a that is comprised between 10 and 100 IU/mL, or with an amount of IFNβ-1b that is comprised between 10 and 100 IU/mL.

5. The method according to claim 1, wherein said blood sample of said individual is incubated in an incubator in vitro at a temperature of 37° C., in the absence of controlling the air composition during incubation.

6. A method for evaluating the in vivo presence of a factor that prevents the biological effect of an IFN-β in an individual that is under treatment of multiple sclerosis with said IFN-β comprising the steps of:
   a. providing a first and a second blood sample of said individual prior to in vivo treatment of said individual with said IFN-β,
   b. adding in vitro to said second blood sample a suitable amount of said IFN-β;
   c. incubating the sample of step a) and step b) in vitro for a suitable period of time;
   d. determining MxA mRNA levels in the incubated first blood sample of step c);
   e. determining MxA mRNA levels in the incubated second blood sample of step c);
   f. comparing MxA mRNA levels determined in step d) and e), and
   g. evaluating the in vivo presence of antibodies directed against an IFN-β in said individual based on the in vitro results obtained in step f).

7. The method according to claim 1, comprising determining mRNA levels of the type I IFN-inducible gene encoding MxA using a kit for evaluating the in vivo presence of antibodies directed against an IFN-β in an individual that is under treatment of multiple sclerosis with said IFN-β, said kit comprising:
   a) a primer pair specific to the mRNA of the Mx1 gene, for the transcription of said mRNA of the Mx1 gene into cDNA and the amplification of the latter,
   b) a probe designed to anneal to an internal region of the produced MxA cDNA,
   c) a control primer pair specific to the mRNA of a control gene which is suitable for the transcription of mRNA of said control gene into cDNA and the amplification of the latter, and
   d) a control probe designed to anneal to an internal region of the produced control cDNA.

* * * * *